US010311575B2

(12) United States Patent
Stofel et al.

(10) Patent No.: US 10,311,575 B2
(45) Date of Patent: Jun. 4, 2019

(54) IMAGING METHOD FOR DETERMINING STRAY FIBERS

(71) Applicant: The Procter & Gamble Company, Cincinnati, OH (US)

(72) Inventors: Samuel Wolfe Stofel, West Chester, OH (US); Lisa Jo Bartz, Singapore (SG); Erica Vencil Buckner, Singapore (SG); Tian Chen, Singapore (SG); Jennifer Mary Marsh, Deerfield Township, OH (US); Supriya Punyani, Singapore (SG); Dana Hance Wolsing, Morning View, KY (US); Brian Xiaoqing Song, Mason, OH (US); Tiffany Tien-Yun Yang, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 176 days.

(21) Appl. No.: 15/467,317

(22) Filed: Mar. 23, 2017

(65) Prior Publication Data

US 2017/0278249 A1    Sep. 28, 2017

Related U.S. Application Data

(60) Provisional application No. 62/312,234, filed on Mar. 23, 2016.

(51) Int. Cl.
*A61B 5/00* (2006.01)
*G06K 9/00* (2006.01)
(Continued)

(52) U.S. Cl.
CPC ............... *G06T 7/13* (2017.01); *A61B 5/448* (2013.01); *G06K 9/00221* (2013.01); *G06T 7/12* (2017.01);
(Continued)

(58) Field of Classification Search
None
See application file for complete search history.

(56) References Cited

U.S. PATENT DOCUMENTS

| 3,709,437 A | 1/1973 | Wright |
| 3,950,532 A | 4/1976 | Bouillon et al. |
| (Continued) | | |

FOREIGN PATENT DOCUMENTS

| CA | 2078375 A1 | 3/1994 |
| CN | 102697668 B | 8/2013 |
| (Continued) | | |

OTHER PUBLICATIONS

Hu Liwen & Ma, Chongyang & Luo, Linjie & Wei, Li-Yi & Li, Hao. (2014). Capturing Braided Hairstyles. ACM Transactions on Graphics. 33. 10.1145/2661229.2661254. (Year: 2014).*

(Continued)

*Primary Examiner* — Kim Y Vu
*Assistant Examiner* — Nathan J Bloom
(74) *Attorney, Agent, or Firm* — Linda M. Sivik (57) ABSTRACT

The present invention is directed to a method of detecting stray fibers emanating from a substrate comprising: a) Taking an image or a series of consecutive images of stray fibers in front of a contrasted background, that is created using one or more light sources, using a digital device; b) Segmenting of stray fibers and background from objects not directly contrasted against the background resulting in a binary image mask; c) Applying an edge detection technique to the image or modification of original image to enhance contrast of stray fibers against the background; and Applying the binary image mask from step b) to an image created in step c) to create an image in which only the stray fibers and/or outline of any other object contrasted against the background are present.

17 Claims, 3 Drawing Sheets

US 10,311,575 B2
Page 2

(51) Int. Cl.
  *G06T 7/12* (2017.01)
  *G06T 7/13* (2017.01)
  *G06T 7/90* (2017.01)
(52) U.S. Cl.
  CPC ...... *G06T 7/90* (2017.01); *G06T 2207/10024* (2013.01)

(56) References Cited

U.S. PATENT DOCUMENTS

| | | | |
|---|---|---|---|
| 3,959,160 | A | 5/1976 | Horsler et al. |
| 4,329,334 | A | 5/1982 | Su et al. |
| 4,839,166 | A | 6/1989 | Grollier et al. |
| 4,867,971 | A | 9/1989 | Ryan et al. |
| 5,294,644 | A | 3/1994 | Login et al. |
| 5,332,569 | A | 7/1994 | Wood et al. |
| 5,364,031 | A | 11/1994 | Taniguchi et al. |
| 5,417,965 | A | 5/1995 | Janchitraponvej et al. |
| 5,635,469 | A | 6/1997 | Fowler et al. |
| 5,747,436 | A | 5/1998 | Patel et al. |
| 5,776,444 | A | 7/1998 | Birtwistle et al. |
| 5,816,446 | A | 10/1998 | Steindorf et al. |
| 5,830,440 | A | 11/1998 | Sturla et al. |
| 5,902,225 | A | 5/1999 | Monson |
| 6,015,780 | A | 1/2000 | Llosas Bigorra et al. |
| 6,020,303 | A | 2/2000 | Cripe et al. |
| 6,039,933 | A | 3/2000 | Samain et al. |
| 6,046,152 | A | 4/2000 | Vinson et al. |
| 6,060,443 | A | 5/2000 | Cripe et al. |
| 6,087,309 | A | 7/2000 | Vinson et al. |
| 6,110,451 | A | 8/2000 | Matz et al. |
| 6,133,222 | A | 10/2000 | Vinson et al. |
| 6,162,834 | A | 12/2000 | Sebillotte-Arnaud et al. |
| 6,268,431 | B1 | 7/2001 | Snyder et al. |
| 6,329,331 | B1 | 12/2001 | Aronson et al. |
| 6,335,312 | B1 | 1/2002 | Coffindaffer et al. |
| 6,423,305 | B1 | 7/2002 | Cauwet-Martin et al. |
| 6,451,300 | B1 | 9/2002 | Dunlop et al. |
| 6,511,669 | B1 | 1/2003 | Garnier et al. |
| 6,579,907 | B1 | 6/2003 | Sebillotte-Arnaud et al. |
| 6,627,585 | B1 | 9/2003 | Steer |
| 6,649,155 | B1 | 11/2003 | Dunlop et al. |
| 6,743,760 | B1 | 6/2004 | Hardy et al. |
| 6,827,795 | B1 | 12/2004 | Kasturi et al. |
| 6,992,054 | B2 | 1/2006 | Lee et al. |
| 7,217,752 | B2 | 5/2007 | Schmucker-Castner et al. |
| 7,220,408 | B2 | 5/2007 | Decoster et al. |
| 7,223,385 | B2 | 5/2007 | Gawtrey et al. |
| 7,485,289 | B2 | 2/2009 | Gawtrey et al. |
| 7,504,094 | B2 | 3/2009 | Decoster et al. |
| 7,531,497 | B2 | 5/2009 | Midha et al. |
| 7,541,320 | B2 | 6/2009 | Dabkowski et al. |
| 7,659,233 | B2 | 2/2010 | Hurley et al. |
| 7,666,825 | B2 | 2/2010 | Wagner et al. |
| 7,820,609 | B2 | 10/2010 | Soffin et al. |
| 7,829,514 | B2 | 11/2010 | Paul et al. |
| 7,928,053 | B2 | 4/2011 | Hecht et al. |
| 7,977,288 | B2 | 7/2011 | SenGupta |
| 8,084,407 | B2 | 12/2011 | Soffin et al. |
| 8,088,721 | B2 | 1/2012 | Soffin et al. |
| 8,124,063 | B2 | 2/2012 | Harichian et al. |
| 8,300,949 | B2 | 10/2012 | Xu |
| 8,401,304 | B2 | 3/2013 | Cavallaro et al. |
| 8,435,501 | B2 | 5/2013 | Peffly et al. |
| 8,437,556 | B1 | 5/2013 | Saisan |
| 8,580,725 | B2 | 11/2013 | Kuhlman et al. |
| 8,609,600 | B2 | 12/2013 | Warr et al. |
| 8,628,760 | B2 | 1/2014 | Carter et al. |
| 8,675,919 | B2 | 3/2014 | Maladen |
| 8,680,035 | B2 | 3/2014 | Kuhlman et al. |
| 8,699,751 | B2 | 4/2014 | Maladen |
| 8,741,363 | B2 | 6/2014 | Albrecht et al. |
| 8,771,765 | B1 | 7/2014 | Fernandez |
| 8,795,635 | B2 | 8/2014 | Tamarkin et al. |
| 8,883,698 | B2 | 11/2014 | Scheibel et al. |
| 9,006,162 | B1 | 4/2015 | Rizk |
| 9,186,642 | B2 | 11/2015 | Dihora et al. |
| 9,258,550 | B1* | 2/2016 | Sieracki .......... G01B 11/24 |
| 9,308,398 | B2 | 4/2016 | Hutton et al. |
| 9,682,021 | B2 | 6/2017 | Tamarkin et al. |
| 9,949,901 | B2 | 4/2018 | Zhao et al. |
| 2001/0000467 | A1 | 4/2001 | Murray |
| 2001/0006621 | A1 | 7/2001 | Coupe et al. |
| 2001/0016565 | A1 | 8/2001 | Bodet et al. |
| 2002/0037299 | A1 | 3/2002 | Turowski-Wanke et al. |
| 2002/0172648 | A1 | 11/2002 | Hehner et al. |
| 2002/0193265 | A1 | 12/2002 | Perron et al. |
| 2002/0197213 | A1 | 12/2002 | Schmenger et al. |
| 2003/0022799 | A1 | 1/2003 | Alvarado et al. |
| 2003/0049292 | A1 | 3/2003 | Turowski-Wanke et al. |
| 2003/0147842 | A1 | 8/2003 | Restle et al. |
| 2003/0180246 | A1 | 9/2003 | Frantz et al. |
| 2003/0185867 | A1 | 10/2003 | Kerschner et al. |
| 2003/0223951 | A1 | 12/2003 | Geary et al. |
| 2003/0228272 | A1 | 12/2003 | Amjad et al. |
| 2004/0014879 | A1 | 1/2004 | Denzer et al. |
| 2004/0184667 | A1* | 9/2004 | Raskar .............. G06T 5/50 382/254 |
| 2004/0235689 | A1 | 11/2004 | Sakai et al. |
| 2005/0020468 | A1 | 1/2005 | Frantz et al. |
| 2006/0002880 | A1 | 1/2006 | Peffly |
| 2006/0057075 | A1 | 3/2006 | Arkin et al. |
| 2006/0079418 | A1 | 4/2006 | Wagner et al. |
| 2006/0079419 | A1 | 4/2006 | Wagner et al. |
| 2006/0079420 | A1 | 4/2006 | Wagner et al. |
| 2006/0079421 | A1 | 4/2006 | Wagner et al. |
| 2006/0090777 | A1 | 5/2006 | Hecht et al. |
| 2006/0120982 | A1 | 6/2006 | Derici et al. |
| 2006/0120988 | A1 | 6/2006 | Bailey et al. |
| 2006/0183662 | A1 | 8/2006 | Crotty et al. |
| 2006/0276357 | A1 | 12/2006 | Smith, III et al. |
| 2007/0072781 | A1 | 3/2007 | Soffin et al. |
| 2007/0154402 | A1 | 7/2007 | Trumbore et al. |
| 2007/0155637 | A1 | 7/2007 | Smith, III et al. |
| 2007/0179207 | A1 | 8/2007 | Fernandez de Castro et al. |
| 2007/0292380 | A1 | 12/2007 | Staudigel et al. |
| 2008/0008668 | A1 | 1/2008 | Harichian et al. |
| 2008/0144895 | A1* | 6/2008 | Hunter .............. G06K 9/00127 382/128 |
| 2008/0206179 | A1 | 8/2008 | Peffly et al. |
| 2008/0247649 | A1* | 10/2008 | Cheng ............... G06T 7/12 382/190 |
| 2008/0260655 | A1 | 10/2008 | Tamarkin et al. |
| 2008/0261844 | A1 | 10/2008 | Ruppert et al. |
| 2008/0317698 | A1 | 12/2008 | Wells et al. |
| 2009/0029900 | A1 | 1/2009 | Cetti et al. |
| 2009/0062406 | A1 | 3/2009 | Loeffler |
| 2009/0148041 | A1* | 6/2009 | Piramuthu ........... G06T 7/11 382/173 |
| 2009/0155383 | A1 | 6/2009 | Kitko et al. |
| 2009/0178210 | A1 | 7/2009 | Bistram |
| 2009/0221463 | A1 | 9/2009 | Kitko et al. |
| 2009/0312224 | A1 | 12/2009 | Yang et al. |
| 2010/0026717 | A1* | 2/2010 | Sato ................. A45D 44/005 345/642 |
| 2010/0316288 | A1* | 12/2010 | Ip .................. G06K 9/38 382/164 |
| 2011/0008267 | A1 | 1/2011 | Arkin et al. |
| 2011/0075926 | A1* | 3/2011 | Piramuthu ........... G06T 7/11 382/173 |
| 2011/0096183 | A1* | 4/2011 | Robertson .......... H04N 5/275 348/222.1 |
| 2011/0110992 | A1* | 5/2011 | Garrison ............ A61K 8/25 424/401 |
| 2011/0165107 | A1 | 7/2011 | Derks et al. |
| 2011/0232668 | A1 | 9/2011 | Hoffmann et al. |
| 2011/0269657 | A1 | 11/2011 | Dihora et al. |
| 2011/0319790 | A1 | 12/2011 | Kost et al. |
| 2012/0014901 | A1 | 1/2012 | Sunkel et al. |
| 2012/0100091 | A1 | 4/2012 | Hata et al. |
| 2012/0250958 | A1* | 10/2012 | Kang ............... A61B 5/1072 382/128 |
| 2012/0316095 | A1 | 12/2012 | Wei et al. |

(56) References Cited

U.S. PATENT DOCUMENTS

| | | |
|---|---|---|
| 2013/0021460 A1* | 1/2013 | Burdoucci ............ A45D 44/005 348/77 |
| 2013/0053295 A1 | 2/2013 | Kinoshita et al. |
| 2013/0053300 A1 | 2/2013 | Scheibel et al. |
| 2013/0115173 A1 | 5/2013 | Trumbore et al. |
| 2013/0143784 A1 | 6/2013 | Rizk |
| 2013/0156712 A1 | 6/2013 | Frantz |
| 2013/0182962 A1* | 7/2013 | Hirakawa ............ G06K 9/4604 382/199 |
| 2013/0189212 A1 | 7/2013 | Jawale et al. |
| 2013/0280192 A1 | 10/2013 | Carter et al. |
| 2013/0280202 A1 | 10/2013 | Stella et al. |
| 2013/0296289 A1 | 11/2013 | Hall et al. |
| 2014/0037703 A1 | 2/2014 | Dihora et al. |
| 2014/0039066 A1 | 2/2014 | Grimadell et al. |
| 2014/0131395 A1 | 5/2014 | Chang |
| 2014/0171471 A1 | 6/2014 | Krueger |
| 2014/0228268 A1 | 8/2014 | Fahl et al. |
| 2014/0237732 A1 | 8/2014 | Zuedel Fernandes et al. |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2015/0021496 A1 | 1/2015 | Shabbir |
| 2015/0098921 A1 | 4/2015 | Franzke et al. |
| 2015/0218496 A1 | 8/2015 | Schmiedel et al. |
| 2015/0297489 A1 | 10/2015 | Kleinen |
| 2015/0313818 A1 | 11/2015 | Stagg |
| 2015/0359725 A1 | 12/2015 | Glenn, Jr. et al. |
| 2016/0008257 A1 | 1/2016 | Zhou et al. |
| 2016/0112616 A1* | 4/2016 | Bonifer ................ H04N 5/2256 348/77 |
| 2016/0113849 A1 | 4/2016 | Grimadell et al. |
| 2016/0193125 A1 | 7/2016 | Jones et al. |
| 2016/0279048 A1 | 9/2016 | Jayaswal et al. |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0354300 A1 | 12/2016 | Thompson et al. |
| 2017/0071837 A1 | 3/2017 | Schelges et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0252273 A1 | 9/2017 | Renock et al. |
| 2017/0278249 A1 | 9/2017 | Stofel et al. |
| 2017/0304172 A1 | 10/2017 | Chang et al. |
| 2017/0304185 A1 | 10/2017 | Glenn, Jr. et al. |
| 2017/0333321 A1 | 11/2017 | Carnali |
| 2018/0057451 A1 | 3/2018 | Owens et al. |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0221266 A1 | 8/2018 | Zhao et al. |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |

FOREIGN PATENT DOCUMENTS

| | | |
|---|---|---|
| CN | 102697670 B | 7/2014 |
| CN | 105769617 A | 7/2016 |
| DE | 4315396 A1 | 11/1994 |
| DE | 202005009618 U1 | 9/2005 |
| EP | 0574086 A2 | 12/1993 |
| EP | 1340485 A2 | 2/2003 |
| EP | 1346720 A2 | 9/2003 |
| EP | 1714678 A1 | 10/2006 |
| EP | 2042216 B1 | 9/2015 |
| JP | H08310924 A | 11/1996 |
| JP | 2964226 B2 | 10/1999 |
| JP | 3069802 B2 | 7/2000 |
| JP | 2002226889 A | 8/2002 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 5667790 B2 | 2/2015 |
| KR | 20140060882 A | 5/2014 |
| WO | WO9325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | WO9924004 A1 | 5/1999 |
| WO | WO0142409 A1 | 6/2001 |
| WO | WO0148021 A1 | 7/2001 |
| WO | WO2005023975 A1 | 3/2005 |
| WO | WO2009016555 A1 | 2/2009 |
| WO | WO2010052147 A2 | 5/2010 |
| WO | WO2012055587 A1 | 5/2012 |
| WO | WO2012084970 A1 | 6/2012 |
| WO | WO2013010706 A1 | 1/2013 |
| WO | WO2014148245 A1 | 9/2014 |
| WO | WO2016147196 A1 | 9/2016 |
| WO | WO2018023180 A1 | 2/2018 |

OTHER PUBLICATIONS

Wikipedia contributors. (Oct. 23, 2018). Hair's breadth. In Wikipedia, The Free Encyclopedia. Retrieved 22:02, Nov. 9, 2018, from https://en.wikipedia.org/w/index.php?title=Hair%27s_breadth&oldid=865354610 (Year: 2018).*
"Natural Detangling Shampoo", Mintel Database, Sep. 13, 2017.
"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 16/156,045.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.
All Final and Non-Final Office Actions for U.S. Appl. No. 15/135,701.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.
All Final and Non-Final Office Actions for U.S. Appl. No. 15/299,860.
All final and non-final office actions for U.S. Appl. No. 15/379,660.
All final and non-final office actions for U.S. Appl. No. 15/379,674.
All final and non-final office actions for U.S. Appl. No. 15/448,911.
All final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.

(56) References Cited

OTHER PUBLICATIONS

All Final and Non-Final Office Actions for U.S. Appl. No. 15/789,172.
All Final and Non-Final Office Actions for U.S. Appl. No. 15/789,188.
All Final and Non-Final Office Actions for U.S. Appl. No. 15/789,208.
All Final and Non-final Office Actions for U.S. Appl. No. 15/923,499.
All final and non-final office actions for U.S. Appl. No. 15/962,327.
All final and non-final office actions for U.S. Appl. No. 15/962,351.
All final and non-final office actions for U.S. Appl. No. 16/001,045.
All final and non-final office actions for U.S. Appl. No. 16/001,053.
All final and non-final office actions for U.S. Appl. No. 16/001,058.
All final and non-final office actions for U.S. Appl. No. 16/001,064.
All Final and Non-Final Office Actions for U.S. Appl. No. 16/156,015.
All Final and Non-Final Office Actions for U.S. Appl. No. 16/156,038.
All Final and Non-Final Office Actions for U.S. Appl. No. 16/156,053.
All Final and Non-Final Office Actions for U.S. Appl. No. 16/156,066.
All Final and Non-Final Office Actions for U.S. Appl. No. 16/156,072.
All final and non-final office actions for U.S. Appl. No. 16/165,016.
All final and non-final office actions for U.S. Appl. No. 16/165,033.
All final and non-final office actions for U.S. Appl. No. 16/165,044.
All final and non-final office actions for U.S. Appl. No. 16/170,498.
All final and non-final office actions for U.S. Appl. No. 16/170,516.
All final and non-final office actions for U.S. Appl. No. 16/170,711.
All final and non-final office actions for U.S. Appl. No. 16/226,914.
All final and non-final office actions for U.S. Appl. No. 16/226,927.
All final and non-final office actions for U.S. Appl. No. 16/248,900.
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018.
Dehyquart Guar: Published Nov. 2010.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved Dec. 20, 2018, p. 1.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 12, 2017.
PCT International Search Report and Written Opinion for PCT/US2017/057497 dated Jan. 8, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.
PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.
PCT International Search Report and Written Opinion for PCT/US2018/036185 dated Aug. 3, 2018.
PCT International Search Report and Written Opinion for PCT/US2018/055102 dated Jan. 9, 2019.
PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/057476 dated Jan. 18, 2019.
Polyquaternium: "Final Report on the Safety Assessment of the Polyguatemium-10", Journal of the American College of Toxicology, Jan. 1, 1988, URL: http://www.beauty-review.nl/wp-content/uploads/2015/02/Final-Report-on-theSafety-Assessment-of-Polyquaternium-10.pdf, retrieved on Dec. 20, 2018.
Practical Modem Hair Science, Published 2012.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.
"Deep Image Matting", Ning Xu et al, Beckman Institute for Advanced Science and Technology, University of Illinois at Urbana-Champaign, Adobe Research, Mar. 10, 2017.

* cited by examiner

IMAGING METHOD FOR DETERMINING STRAY FIBERS

FIELD OF THE INVENTION

The present invention relates to a method for determining stray fibers using imaging techniques.

BACKGROUND OF THE INVENTION

Frizz and fuzz are common terms in the hair and textile industry, respectively (among others), to describe the presence of stray fibers amongst a substrate. The ability to measure these phenomena under a variety of lighting conditions is desirable, such as allowing a person to use a device, such as a smartphone or tablet as an evaluation tool. Such a tool could be used to help recommend a product, styling technique, or laundry machine settings (among others). In an environment where the lighting conditions are highly controlled, this can be accomplished using a common technique involving the use of backlighting and applying fundamental edge detection filters. The difficulty lies in extending this capability to a situation in which an object containing stray fibers is imaged against a contrasted background with little to no control over the surrounding illumination. In the example of imaging the frizz on a person, backlighting alone followed by fundamental edge detection algorithms can yield satisfactory results (an image in which only the fibers directly contrasted against the background are emphasized), however if any part of the face is illuminated from the front, contrasting regions of the face will be detected by the edge detection technique and create unwanted artifacts in the stray fiber image. The methodology described herein allows for the creation of a foundational stray fiber image taken under a variety of lighting conditions that can be subsequently analyzed for the detection, quantification, and virtual alteration of stray fibers when the starting image is one containing stray fibers emanating from an object/substrate and contrasted against a background.

SUMMARY OF INVENTION

In an embodiment, the present invention is directed to a method of detecting stray fibers emanating from a substrate comprising: a) Taking an image or a series of consecutive images of stray fibers in front of a contrasted background, that is created using one or more light sources, using a digital device; b) Segmenting of stray fibers and background from objects not directly contrasted against the background resulting in a binary image mask; c) Applying an edge detection technique to the image or modification of original image to enhance contrast of stray fibers against the background; and Applying the binary image mask from step b) to an image created in step c) to create an image in which only the stray fibers and/or outline of any other object contrasted against the background are present.

DETAILED DESCRIPTION OF EMBODIMENTS OF THE INVENTION

All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

Segmenting—The process employed by which pixels are assigned to a class. Pixels with the same class share similar characteristics. The shared characteristics dependent upon the process employed. In a non limiting example, an image may be segmented into two classes; stray fiber and non-stray fiber pixels.

Thresholding—A segmentation technique in which each pixel intensity is compared to one or more reference intensity levels and subsequently placed into classes; in a non-limiting example, an image in which the pixel is classified as stray fiber or background if the pixel intensity of the hue color channel is between $X_1$ and $X_2$, otherwise the pixel is classified as a non-hair and non-background pixel.

Stray Fiber—Fibers that extend from a substrate against a contrasted background. The fibers may intentionally extend beyond the substrate by design (such as to enhance the texture of a surface) or be unintentional or undesired (as is mostly the case for frizz and fuzz examples).

Edge Detection Technique—An image analysis technique used to find or enhance spatial intensity differences that change rapidly.

The present invention can comprise, consist essentially of, or consist of, the essential components as well as optional components, features or elements described herein. As used herein, "consisting essentially of" means that the component may include additional features or steps, but only if the additional components or steps do not materially alter the basic and novel characteristics of the claimed methods.

Figure 1A:
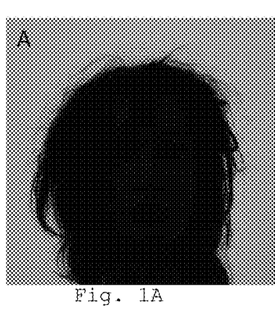
FIG. 1A is an image of a frizzy haired mannequin head imaged with purple backlit background.
Figure 1B:
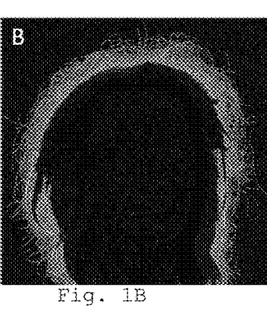
FIG. 1B is an image of stray fibers detected using a Laplacian edge detection algorithm yielding satisfactory results.
Figure 1C:
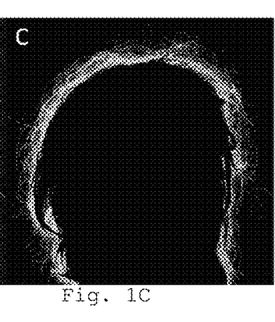
FIG. 1C is an image of stray fibers detected using a threshold range. Results not as successful as edge detection algorithm image depicted in FIG. 1B but still yielding satisfactory results.
Figure 2A:
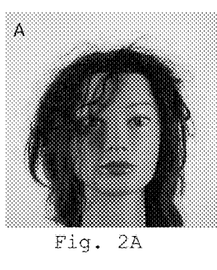
FIG. 2A is an image of the same frizzy haired mannequin head and purple backlit background imaged in 1A, further with the addition of two front lights.
Figure 2B:
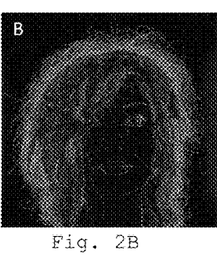
FIG. 2B is an image created using the same Laplacian edge detection algorithm used in 1B. The result continues to detect the stray fibers, and further the bulk hair and facial features have also been detected.

The detection and quantification of stray hair fibers amongst a hair tress assembly using a contrasting backlit background is a routine method within the hair industry as a means to assess product performance. FIG. 1A is an example of a frizzy medium brown mannequin head with a contrasting purple backlit background. Either edge detection or threshold ranges can segment the hair fibers from the background allowing for both qualitative and quantitative assessments (see FIGS. 1B and 1C, respectively). A natural non-limiting extension is the desire to perform similar types of assessments in vivo in which the lighting conditions are not nearly as controlled yet the hair fibers are still contrasted against a background. A non-limiting example would be a person taking an image of themselves under ambient lighting against a contrasted background. The techniques that worked well under controlled backlit conditions may produce undesirable results in scenarios in which the lighting conditions are not highly controlled. As a non-limiting example of some of the difficulties encountered, two off-center front lights are added to the imaging setup used to capture the same mannequin head and purple backlit background depicted in FIG. 1A (See FIG. 2A). The edge detection algorithm used to create a successful stray fiber image when the mannequin head is only backlit and is applied to the front lit mannequin head. It had been thought that the intensity contrast between the stray fibers and the local background should allow for successful segmentation of the two classes across the entire image. A successful segmentation of the fibers and background is achieved by applying a 9×9 Laplacian kernel to the entire image, however, the facial features and contrasting elements of the bulk hair are also detected as seen in FIG. 2B. Multiple edge detection algorithms is attempted including Sobel, Roberts, and Variance. All exhibit similar inability to only detect the stray fibers contrasted against the background.

Figure 2C:
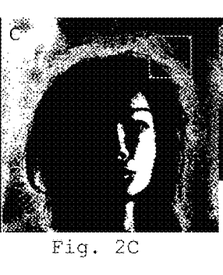
FIG. 2C is an image created by using a threshold range based on the intensity of the Level channel revealed successful stray fiber detection in some localized areas of the image (see FIG. 2D), but does not yield satisfactory result across the entire image.
Figure 2D:
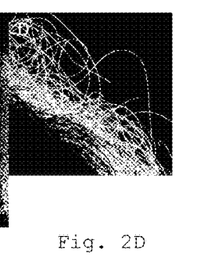
FIG. 2D is a close up view of the area indicated by the box in FIG. 2C.

Another standard technique that can be successful with objects that are only backlit is the use of a threshold range. wherein is to apply a global threshold range across the entire image using the Level color channel of the HSL color space (Hue Saturation Level). It could be expected that the stray hair fibers should have a pixel intensity that is lower in value than the contrasting background. In localized areas of the image, the stray fibers can be successfully segmented from the background, however not possible across the entire image (see FIG. 2C). In this lighting configuration the intensity of the background pixels is not universally uniform causing overlap in pixel intensities that represent the background and those that represent the stray fibers. Threshold ranges can also be attempted across other individual color channels and combinations thereof; each attempt resulting in a failure to segment only the stray fibers due to an overlap in pixel intensities between the background and stray fibers. Thus neither of the standard techniques on their own is able to isolate the stray hair alone from the background while excluding the stray hair and other features of the face.

Figure 3A:
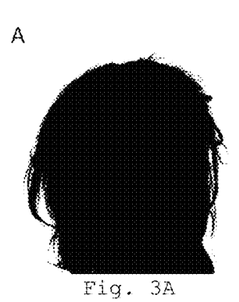
FIG. 3A is an image created using a threshold range applied to FIG. 2A to segment the background+stray fiber together from everything else in the image.
Figure 3B:
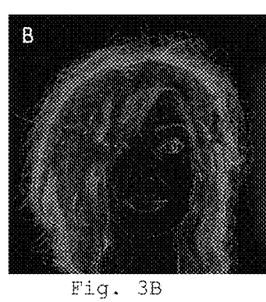
FIG. 3B is an image created using an edge detection algorithm (Laplacian) applied to FIG. 2A.
Figure 3C:
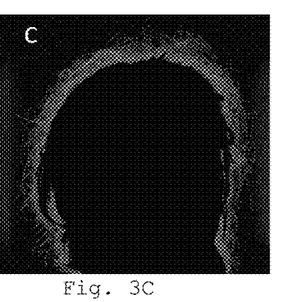
FIG. 3C is stray fiber image created by using FIG. 3A as a mask applied to FIG. 3B. The result is an image in which only the stray fibers are accentuated and all other image features are suppressed or masked out completely.

It has become clear that a novel approach is needed. In attempting these different techniques, it has been noticed that the intensities of the pixels representing the stray fibers are very similar in color to the background pixels. As the background is changed, so does the pixel intensities of the stray fiber pixels. In every case, the stray fiber pixel intensities are influenced by the background color and intensity. It is also noticed that other elements of the image not directly contrasted against the background, the face and bulk hair color for example, are only minimally influenced, if at all, by the background color and intensity. By taking advantage of this observation, it has been realized that a contrasting background can be used to drive the pixel intensities of the stray fibers far enough away from the pixel intensities of the other objects in the image (face and bulk hair, for example), that a segmentation technique, thresholding being a non-limiting example, can be used to segment the image into two classes: one class being the background and stray hair fibers over the background and the other class being the face and bulk hair (See FIG. 3A). The second class is used as a mask on the edge detected image resulting in an image in which only the stray fibers contrasted against the background are accentuated and other objects in the image not directly contrasted by the background are masked out (see FIG. 3C). In general, the present invention is able to create a stray fiber image under a variety of illumination conditions by taking advantage of the observation that the pixel intensities representing the stray fibers are influenced by the background color and intensity while the pixels representing other elements of the image not directly contrasted against the background are not as easily changed. This methodology relies on both the color mixing of the optical signals from the background and fiber and the spatial mixing of signals needed to do edge detection. The intensity image is thresholded to produce a mask that is applied to the edge detected image so that only stray fibers over the contrasted background are visible while other fibers and features of the image are masked away. The mixing of the background and stray fiber signals can be created in a number of ways including but not limited to using transparent fibers, purposefully defocusing the lens, acquiring images at a low resolution, digital image processing, and cross-talking of pixels within the imaging sensor.

There are numerous examples where the detection and quantification of stray fibers amongst a substrate against a contrasting background under a variety of illumination conditions is desired. In an embodiment of the present invention, the method includes the following: 1) Taking an image or series of consecutive images of stray fibers in front of a contrasted background that is either created using one or more light sources and captured using a digital device of which a camera and video camera are two non-limiting examples; 2) Segmenting of stray fibers and background together from objects of non-interest resulting in a binary image mask; 3) Applying edge detection technique to the original image or modification of original image to enhance contrast of stray fibers against the background; 4) Applying binary mask from step 2 to the resulting image from step 3 yielding a stray fiber image in which only the stray fibers directly contrasted against the background are accentuated and the other object in the image not directly contrasted against the background are removed from the stray fiber image. The resulting stray fiber image can then be subsequently analyzed to quantify the presence of, enhance visibility of, or foundation to creating virtual alterations of (among others) stray fibers in front of a contrasted background Some alternative components to the present invention have been identified. More optimized results may be obtained under the following circumstances:
1) The edge detection can be done equivalently in either the Fourier domain or in the spatial domain and the size of the filter window should be adjusted so that only one edge per fiber is detected. For example if one is scanning with a window that is too small in the spatial domain, the result is an edge on either side of the fiber, instead of a single edge in the middle.
2) Fibers are sufficiently transparent so that the edges of the stray fibers may be difficult to detect relative to the noise of the contrasted background. In this situation it may be beneficial to illuminate the sample in such way to increase the contrast between the stray fibers and background. For example, the color and intensity of the frontal and/or background illumination may be altered to enhance the contrast of the fibers.

3) Contrasted background may contain a level of noise such that the edge detection algorithm detects edges with the same level of contrast as the edges of the stray fibers. Taking multiple images and averaging them together would reduce the level of noise and enable better edge detection.

Method of Use Examples

The present invention may be useful for quantifying frizz and flyaway for hair, fuzz for fabrics, pilling on fabric. In an embodiment of the present invention, it may be used in marketing and advertising to demonstrate product benefits. In an embodiment of the present invention, it may be used for in-store consultation/demonstrations. In a further embodiment of the present invention, it may be used as a foundation image to create virtual representations of hair with various degrees of frizz and/or flyaway fibers. In an embodiment of the present invention, it may be used for cellulose fiber analyses of, for example, paper products, non limiting examples such as paper towels or toilet tissue or feminine hygiene products.

A further embodiment involves a photograph of a hair switch, non-limiting examples including a straight hair switch, a braid, twisted, curled or other hair switch configurations. A further embodiment of this method may include hair on skin, or hair as part of an eyelash. Yet another embodiment of this method involves detecting the fuzz of a textile material contrasted against a background in which the textile material is comprised of one or a blend of multiple fiber types and/or colors. Yet another embodiment would be to utilize a mobile phone app as a means of self-diagnosis for level of stray fibers or frizz or other related attributes. An embodiment in which, with sufficient computer power, be able to create stray fiber images and/or quantification in real time (on "live" video) allowing for the creation of a virtual mirror. Another embodiment would be to look at efficacy of hair removal on the body or face. In an embodiment of the present invention the stray fiber may have a diameter of 0.25 inches or less. In a further embodiment, the stray fiber may have a diameter of 0.10 inches of less. In a further embodiment, the stray fiber may have a diameter of 0.05 inches of less. In an embodiment, if the stray fiber is a fabric fiber, the fabric fiber may have a diameter of less than 50 microns; in an embodiment, the fabric fiber may have a diameter less than 25 microns; in a further embodiment, the fabric fiber may have a diameter less than 10 microns.

Method
Image Capture
1. Object containing stray fibers to be imaged is placed between the camera and highly contrasted background.
2. In an embodiment of the present invention the background can be uniform across the entire image area and consisting of a color and intensity to provide as much contrast between the stray fibers and the background as possible. Moderate color and intensity gradients within the background can be tolerated with this technique so long as the high degree of contrast between the stray fiber and background is maintained. The background can also be chosen such that it does not share any of the same color as the object being imaged. This will allow the parts of the object that are not directly contrasted against the background to be masked out. Should, in the resulting image, the background and parts of the object not contrasted against the background share the same pixel colors/intensities, then a mask could be drawn manually or automatically added should the position and approximate size of the object be known. A non-limiting example could be using facial recognition to determine the location and size of the face as a means to draw a mask.
3. Once the background is chosen, the camera is focused on the stray fibers. If the stray fibers extend beyond the depth of field, then multiple images can be taken at different focal points and combined into a single image using a technique in order to achieve an image that is entirely in focus.
4. Next, the camera aperture is chosen to maximize the contrast between the stray fibers and background. This can be achieved by applying an edge detection filter to the image and manipulating the aperture until the edges that define the hair fibers against the background have reached a maximum intensity.
5. The ISO or gain is chosen to be as small as possible to minimize noise in the resulting image. If motion blur is a potential issue, then it can be considered to illuminate the background with more light.
6. The exposure time is chosen such that the resulting pixels intensities are typically below being overexposed so as to maximize the contrast present in the image.
7. Next—an image can be captured.

Image Analysis
1. A segmentation technique is used to separate the background and stray fibers from the rest of the objects not contrasted against the background. For cases in which the background and stray fibers do not share any of the same pixel colors as any of the other pixels, a simple threshold can be applied to the image to create a binary mask in which the background and stray fibers are colored white (1) and the objects not contrasted against the background colored black (0). In instances where there are shared pixel colors, the mask can be manually edited or an automatic mask can be applied to the binary image if the locations of the object(s) not contrasted against the background are generally or exactly known (see FIG. 3A).
2. In parallel, an edge detection algorithm is applied to the raw image. The edge detection filter may be sized to fit the diameter of the stray fibers being investigated. For example, quality results have been achieved using a 9×9 laplacian filter for stray fibers with a diameter of up to 5 pixels in the raw image. (See FIG. 3B)
3. Next the binary mask from step 1 is applied to the edge detection image created from step 2 resulting in an image in which only objects that are contrasted against the background are emphasized (see FIG. 3C).
4. The resulting image is referred to as the stray fiber image and can be subsequently analyzed/manipulated to enhance the detection of, amount of, or use in virtual manipulations of stray fibers.

Quantification
1. The stray fiber image from step 4 of the Image Analysis process can be converted to a binary image by applying a single threshold. The resulting binary image can be quantified by counting the number of pixels, however a weighted counting algorithm (like bwarea, MATLAB) may be used or other conventional algorithm software.

In an embodiment of the present invention, a potential fiber in the image that is not connected to the stray fibers, or within a specified distance of another stray fiber, may be considered as noise and excluded from the final image. In a further embodiment, a potential fiber in the image that is not fiber shaped, such as a round object instead of a line-like object, may be considered as noise and excluded from the final image. In yet a further embodiment, a potential fiber in the image that does not exceed a minimum allowable area, for example and object only 2 pixels in size, may be considered as noise and excluded from the final image.

EXAMPLES

In an embodiment of the present invention, the following are non-limiting examples showing different light configuration A non limiting example of the present invention is as follows. A mannequin head is placed with front lit using 2 fluorescent light source on either side of the face. A purple backlight is used to provide a contrasting background. A Nikon D5200 with VR 18-55 mm f/3.5-5.6 G lens at to a focal length of 26 mm, aperture of f/8, exposure time of ½5 seconds, and ISO of 100 is used to capture an image of the mannequin head.

In an embodiment of the present invention, this method can be successfully applied to fibers of multiple colors, or even lacking pigment altogether so long as the contrast of the fiber against the background is maintained.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

All documents cited in the Detailed Description of the Invention are, in relevant part, incorporated herein by reference; the citation of any document is not to be construed as an admission that it is prior art with respect to the invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method of detecting stray fibers emanating from a substrate comprising:
    a) Taking an image or a series of consecutive images of stray fibers in front of a contrasted background, that is created using one or more light sources, using a digital device;
    b) Segmenting of stray fibers and background from objects not directly contrasted against the background resulting in a binary image mask;
    c) Applying an edge detection technique to the image from 1a) or modification of the image of 1a) to enhance contrast of stray fibers against the background;
    d) Applying the binary image mask from step b) to an image created in step c) to create an image in which the stray fibers and/or outline of any other object contrasted against the background are present.

2. Method of claim 1 wherein step b) the segmentation technique is a single threshold constant or combination of threshold constants that define intensity ranges.

3. Method of claim 1 wherein step c) the edge detection technique is a Laplacian, Canny, Sobel, Robertson, Prewitt, high pass filtering or any other type of edge detection filter.

4. Method of claim 1 wherein step d) is followed by manipulating the stray fiber image by adjusting one or more of the following parameters; gamma, contrast, brightness to enhance the appearance the stray fibers against the background pixels.

5. Method of claim 1 wherein step d) is followed by segmenting of the image to enhance the appearance the stray fibers against the background pixels.

6. Method of claim 1 wherein the stray fiber image or a further manipulated version of the stray fiber image is used as a basis for quantifying the amount of stray fibers in the image.

7. Method of claim 1 wherein the stray fiber image or a further manipulated version of the stray fiber image is used as a basis for performing additional visualizations of the original image.

8. Method of claim 1 wherein the stray fibers are from the group consisting of hair, fabrics, cellulosic substrate, non-cellulosic and mixtures thereof.

9. Method of claim 8 wherein the hair is attached to a person.

10. Method of claim 8 wherein the hair is a hair tress.

11. Method of claim 10 wherein the hair tress is a braided tress.

12. Method of claim 1 step a) wherein the device is a color or monochrome digital camera that can be used to capture video or still images.

13. Method of claim 1 step a) wherein a color of the background is chosen to be different than the color of any other objects not directly contrasted against the background.

14. Method of claim 1 wherein the stray fiber has a diameter of 0.25 inches or less.

15. Method of claim 1 wherein the one or more light sources can be in a position selected from the group consisting of front, side, top, bottom, back or mixtures thereof.

16. Method of claim 8 wherein the hair or hair tress is twisted/rotated.

17. Method of claim 1, wherein object not directly contrasted against the background is masked out by a mask that is drawn manually or automatically added should the position and approximate size of the object be known.

* * * * *